United States Patent
Hoyme et al.

(10) Patent No.: US 8,798,760 B2
(45) Date of Patent: *Aug. 5, 2014

(54) SYSTEM AND METHOD FOR REMOTELY PROGRAMMING A PATIENT MEDICAL DEVICE

(71) Applicant: Cardiac Pacemakers, Inc., St. Paul, MN (US)

(72) Inventors: Kenneth P. Hoyme, Plymouth, MN (US); Karen Franke, Tampa, FL (US); George D. Jelatis, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/073,495

(22) Filed: Nov. 6, 2013

(65) Prior Publication Data

US 2014/0055230 A1    Feb. 27, 2014

Related U.S. Application Data (63) Continuation of application No. 11/651,118, filed on Jan. 8, 2007, now Pat. No. 8,588,912.

(60) Provisional application No. 60/757,399, filed on Jan. 9, 2006, provisional application No. 60/761,462, filed on Jan. 24, 2006.

(51) Int. Cl.
*A61N 1/36* (2006.01)

(52) U.S. Cl.
USPC .......................................... 607/59

(58) Field of Classification Search
CPC .......... A61N 1/37211; A61N 1/37235; A61N 1/37252–1/37282
USPC ................................ 607/30, 31, 59
See application file for complete search history.

(56) References Cited

U.S. PATENT DOCUMENTS 6,024,699 A    2/2000  Surwit et al.
6,083,248 A    7/2000  Thompson et al.
(Continued)

FOREIGN PATENT DOCUMENTS

EP    1478432    11/2004
WO    00/29064    5/2000
(Continued)

OTHER PUBLICATIONS

Communication Pursuant to Article 94(3) EPC, for European Patent Application No. 07716390.5, mailed Jan. 22, 2014 (7 pages).

(Continued)

*Primary Examiner* — George Evanisko
(74) *Attorney, Agent, or Firm* — Pauly, DeVries, Smith & Deffner LLC (57) ABSTRACT

A system and method for remotely programming a patient medical device (PMD) is presented. Programming instructions specified remotely are translated into commands formatted for a PMD to control functionality thereof. Correctness of the PMD-formatted commands is checked. Patient consent to modify the functionality of the PMD is confirmed. Application of the PMD-formatted commands to the PMD is controlled during a programming session initiated and performed remotely. The application of the PMD-formatted commands is confirmed through interrogation of the PMD to verify the functionality modified.

20 Claims, 6 Drawing Sheets

(56) References Cited

U.S. PATENT DOCUMENTS

| | | | |
|---|---|---|---|
| 6,168,563 | B1 | 1/2001 | Brown et al. |
| 6,171,256 | B1 | 1/2001 | Joo et al. |
| 6,308,099 | B1 | 10/2001 | Fox et al. |
| 6,336,903 | B1 | 1/2002 | Bardy |
| 6,368,284 | B1 | 4/2002 | Bardy |
| 6,398,728 | B1 | 6/2002 | Bardy |
| 6,411,840 | B1 | 6/2002 | Bardy |
| 6,416,471 | B1 | 7/2002 | Kumar et al. |
| 6,440,066 | B1 | 8/2002 | Bardy |
| 6,497,655 | B1 | 12/2002 | Linberg et al. |
| 6,512,954 | B2 | 1/2003 | Fox et al. |
| 6,792,311 | B2 | 9/2004 | Fox et al. |
| 6,827,670 | B1 | 12/2004 | Stark et al. |
| 6,880,085 | B1 | 4/2005 | Balczewski et al. |
| 7,027,872 | B2 | 4/2006 | Thompson et al. |
| 7,060,031 | B2 | 6/2006 | Webb et al. |
| 7,493,165 | B2 | 2/2009 | Fox et al. |
| 7,565,197 | B2 | 7/2009 | Haubrich et al. |
| 8,588,912 | B2 * | 11/2013 | Hoyme et al. ............ 607/31 |
| 2006/0253301 | A1 | 5/2006 | Simms et al. |

FOREIGN PATENT DOCUMENTS

| | | |
|---|---|---|
| WO | 02/074386 | 9/2002 |
| WO | 2004/070994 | 8/2004 |
| WO | 2005/056087 | 6/2005 |
| WO | 2005/057879 | 6/2005 |
| WO | 2007/081829 | 7/2007 |

OTHER PUBLICATIONS

E. Hammond, "National Committee on Vital and Health Statistics, Subcommittee on Health Data Needs, Standards and Security," http://www.ncvhs.hhs.gov/970211t3.htm, pp. 1-4 (Feb. 11, 1997).

European Examination Report, "Communication pursuant to Article 94(3) EPC", European Patent Office, mailed Dec. 5, 2008, for EP Application No. 07715390.5, corresponding to U.S. Appl. No. 11/651,118 (6 pages).

File History from co-owned, U.S. Appl. No. 11/651,118, As downloaded from USPTO PAIR on Mar. 11, 2014, 306 pages.

Health Insurance Portability and Accountability Act of 1996, Pub. L. No. 104-191, 110 Stat. 1936 (Aug. 21, 1996).

"Japanese Office Action", for Japanese Application No. 2008-549579, corresponding to U.S. Appl. No. 11/651,118, mailed Nov. 29, 2011, (pp. 61) Including English translation., 61.

PCT International Preliminary Report and Written Opinion from International Application No. PCT/US2007/000325, corresponding to U.S. Appl. No. 11/651,118, mailed Jul. 24, 2008 (8 pages).

Security and Electronics Signature Standards; Proposed Rule, Federal Register, vol. 63, No. 155 (Aug. 12, 1998).

W. Diffie, "The First Ten Years of Public-Key Cryptography," Proceedings of the IEEE, vol. 76, No. 5, pp. 560-577 (May 1988).

* cited by examiner

SYSTEM AND METHOD FOR REMOTELY PROGRAMMING A PATIENT MEDICAL DEVICE

CROSS-REFERENCE TO RELATED APPLICATION

This application is a continuation of U.S. patent application Ser. No. 11/651,118, issued on Nov. 19, 2013 as U.S. Pat. No. 8,588,912; which claims priority under 35 USC §119(e) to U.S. provisional patent application, Ser. No. 60/757,399, filed Jan. 9, 2006 and U.S. provisional patent application, Ser. No. 60/761,462, filed Jan. 24, 2006, the disclosures of which are incorporated by reference.

FIELD OF THE INVENTION

The invention relates in general to medical device programming and, specifically, to a system and method for remotely programming a patient medical device.

BACKGROUND OF THE INVENTION

The Food & Drug Administration (FDA) categorizes medical devices into three classes based on medical regulations and federal law. Class III medical devices are subject to continuing regulatory control and can only be interrogated and programmed under the supervision of licensed medical caregivers. Class III medical devices include implantable medical devices (IMDs), such as cardiac pacemakers, defibrillators, and cerebella stimulators, and certain types of external medical devices (EMDs), such as automatic external defibrillators (AEDs).

Historically, the interrogation and programming of Class III medical devices had to be performed in a clinic or hospital using FDA-regulated programmer recorders, which use inductive or, more recently, wireless telemetry, such as radio frequency (RF) telemetry, to retrieve patient data and device settings and to apply new programming. Clinic visits, though, incur time, expense, and inconvenience, even when modest. Thus, to improve patient care, patient-operable monitors, such as repeaters, were developed to enable caregivers to remotely access their patients' medical devices outside of a clinic or hospital. These monitors can remotely retrieve patient data and device settings, which are periodically delivered to a repository for caregiver consideration and archival.

Despite their convenience, patient-operable monitors are not presently permitted to program medical devices for reasons of patient safety and regulatory compliance. For instance, programming cannot be performed by a non-FDA-regulated device, so any remote programming must currently include interfacing through a device that is properly regulated. As well, some device parameters are used to test device operation in situ and can be potentially life-threatening. Consequently, these parameters must only be modified in-clinic with life safety equipment and trained medical personnel in attendance. Finally, patient consent is implied when programming is performed in-clinic, but must be explicitly secured before remote programming is attempted. Conventional approaches fail to adequately address these issues.

For instance, U.S. Pat. No. 7,060,031 issued Jun. 13, 2006 to Webb et al., discloses a system and method for remotely programming IMDs. Pending programming requests are placed in a request queue that is ordered from older to most recent request. The requests can be encrypted and assigned sequence numbers that enable a remote monitor to determine that the request is later in sequence than any earlier requests previously applied to the IMD. Webb, however, assumes fully regulated infrastructure to effect remote programming. Moreover, such an infrastructure is costly to deploy and may not be available when a physician is called upon to make programming changes.

Therefore, there is a need for an approach to performing remote medical device programming that assures both patient safety and compliance without requiring a regulated environment as the only means to specify programming.

SUMMARY OF THE INVENTION

A system and method for enabling caregivers to perform programming of patient medical devices (PMDs), either IMDs or EMDs, remotely includes a pair of control zones to logically separate regulated and non-regulated components. Caregivers can specify programming instructions using non-regulated components, such as a dedicated application executing on a personal computer or a Web client, or regulated components, such as a remotely-connectable programmer. The programming instructions can be specified in real time or deferred time. The caregivers are only able to select those programming instructions that specify operations which can be performed safely when the patient is not in the presence of a caregiver, to avoid endangering the patient. Programming instructions that originate in the non-regulated control zone are forwarded through the servers into the regulated control zone. Each programming instruction is translated into commands formatted in PMD representation, which are checked for correctness. The PMD-formatted commands are digitally signed by a trusted server. The PMD-formatted commands are converted into a simple Web page or displayable representation, which is sent back to the caregiver to review for accuracy. Upon caregiver approval, the PMD-formatted commands are marked for delivery to the remote programming device (RPD). The PMD-formatted commands are verified by the RPD, the IMD, or both devices, for authenticity and integrity. If successfully verified, the PMD-formatted commands are applied to the PMD. The PMD is then interrogated to retrieve post-programming data for confirmation and caregiver review.

One embodiment provides a system and method for remotely programming a patient medical device (PMD). Programming instructions specified remotely are translated into commands formatted for a PMD to control functionality thereof. Correctness of the PMD-formatted commands is checked. Patient consent to modify the functionality of the PMD is confirmed. Application of the PMD-formatted commands to the PMD is controlled during a programming session initiated and performed remotely. The application of the PMD-formatted commands is confirmed through interrogation of the PMD to verify the functionality modified.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Although described here in relation to IMDs and EMDs intended for providing cardiac and cardiopulmonary therapy and monitoring, the embodiments described apply generally to all forms of patient medical devices capable of being remotely interrogated and programmed.

Remote Programming System

Figure 1:
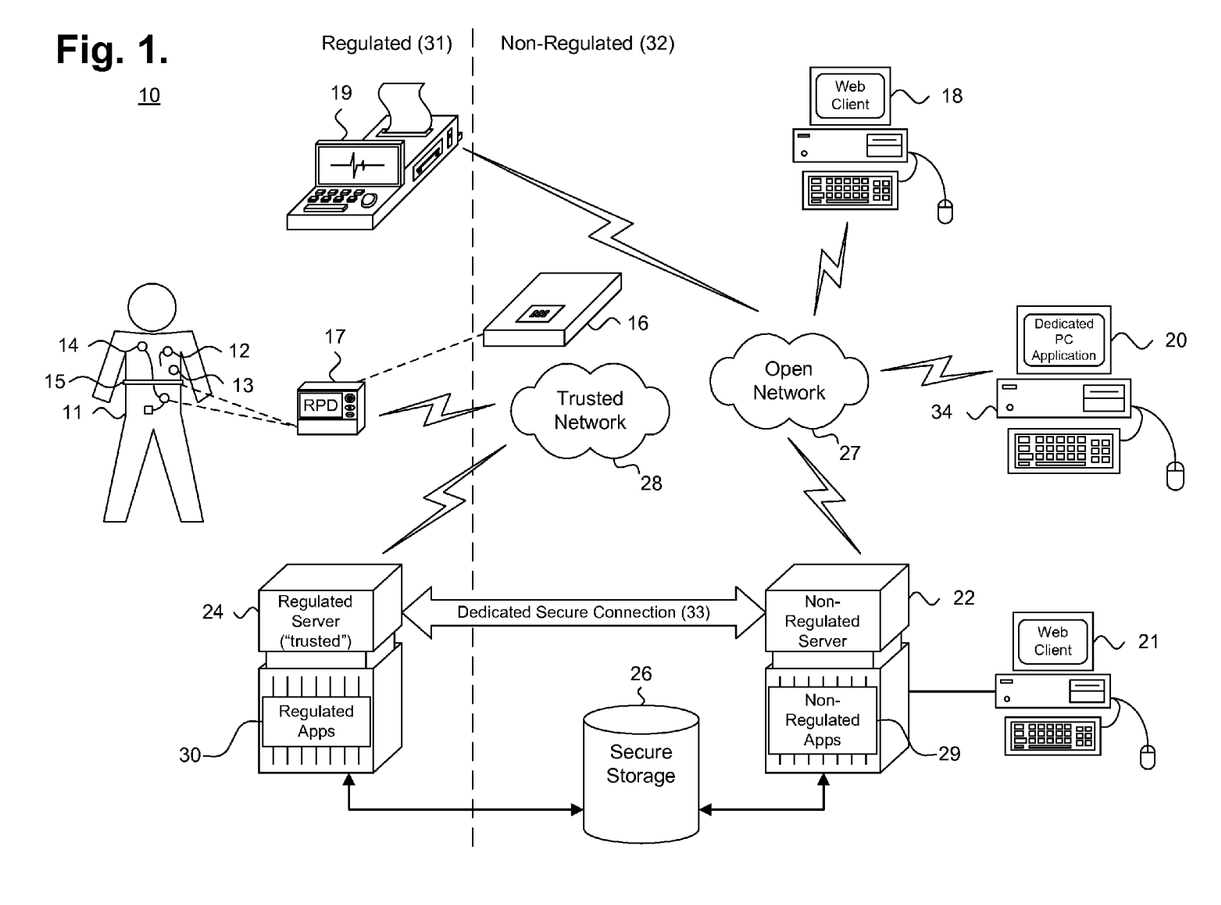
FIG. 1 is a block diagram showing, by way of example, a system for remotely programming a patient medical device, in accordance with one embodiment.

Fundamentally, the remote programming of PMDs requires logically separating components that must be kept in compliance with FDA and other applicable patient care regulations and guidelines from other components. Remote programming also requires establishing and managing reliable, safe, and trustworthy cooperation among all of these components. FIG. 1 is a block diagram showing, by way of example, a system 10 for remotely programming a patient medical device, in accordance with one embodiment. The system 10 includes control zones 31, 32 that logically separate system components into two groups. The regulated and non-regulated control zones 31, 32 logically, but not physically, separate those devices and applications that must be controlled for compliance from those that do not. Regulated control zone 31 contains regulated medical devices and applications, such as Class III medical devices and regulated software applications executing on a server platform. Non-regulated control zone 32 contains those system components that are not regulated. A component that includes both regulated and non-regulated aspects is grouped into the regulated control zone 31.

The regulated control zone 31 includes four loosely grouped sets of components. First, caregivers are able to specify programming instructions for a PMD using either a data entry mechanism in the non-regulated control zone 32 or through a regulated but remotely-connectable data entry mechanism in the regulated control zone 31, such as a remotely-connectable programmer 19. Other regulated data entry mechanisms are possible. All PMDs are also grouped into the regulated control zone 31 and include IMDs 12, such as pacemakers, implantable cardiac defibrillators (ICDs), drug pumps, and neuro-stimulators; EMDs 14, such as automatic external defibrillators (AEDs); implantable sensors 13, such as heart and respiratory monitors and diagnostic multi-sensor non-therapeutic devices; and external sensors 15, such as Holter monitors. Other types of implantable or external PMDs for therapeutic, diagnostic, or other medical purpose are possible. Each patient 11 having a PMD 12-15 that is suitable for remote programming has an RPD 17, such as a repeater or patient communicator, which is a form of regulated device that enables caregivers to remotely access their patients' PMDs outside of a clinic or hospital. Finally, each RPD 17 receives digitally signed PMD-formatted commands from a regulated server 24, which is trusted in the sense of data security and is capable of supporting regulated component execution, including regulated software applications 30, or directly from a regulated data entry mechanism, such as a remotely-connectable programmer 19. The regulated server 24 communicates with the RPD 17 over a trusted network 28 and with components in the non-regulated zone 32 via a dedicated secure connection 33 to a non-regulated server 22. Other regulated system components are possible.

The non-regulated control zone 32 includes all other components, including non-regulated data entry mechanisms, servers, and PMDs. For instance, caregivers are able to specify programming instructions using a remote Web client 18, a dedicated application 20 executing on a personal computer 34, or local Web client 21. Programming instructions that originate from any of these non-regulated data entry mechanisms, as well as from remotely-connectable regulated data entry mechanisms, must be forwarded to the regulated server 24 through a non-regulated server 22 that is connected via an open network 27. Finally, PMDs that are not regulated, such as a weight scale 16 or blood pressure cuff (not shown), do not generally affect patient safety and can be grouped as part of the non-regulated control zone 32. Other non-regulated system components are possible.

The regulated server 24 and non-regulated servers 22 serve as a gateway between the regulated and non-regulated control zones 31, 32, and exchange messages over a dedicated secure connection 33. The regulated server 24 is able to run regulated applications 30, whereas the non-regulated server 22 does not. However, the non-regulated server 22 can execute a wider range of non-regulated applications 29, such as a Web server (not shown) for providing Web content to the Web clients 18, 21. The functionality of the regulated and non-regulated servers 22, 24 can be hosted physically on the same hardware platform, but the execution of and any modifications to the regulated applications 30 must remain controlled for compliance. The regulated and non-regulated servers 22, 24 also share access to secure storage 26, in which patient data and other information can be safely stored. Other server and storage functionality are possible.

Network-capable components in the regulated control zone 31 rely on a trusted network 28, while network-capable components in the non-regulated control zone 32 communicate via an open network 27 or, in a further embodiment, via the trusted network 28. The trusted network 28 is a private wide area network and can include both conventional wired and wireless secure interconnectivity. The open network 27 is a non-private wide area network, such as the Internet, that can similarly include both conventional wired and wireless interconnectivity. In a further embodiment, the trusted network 28 can operate over a public wide area network; however, communications must be encrypted or otherwise protected to ensure patient privacy and to guard against compromise or interference, such as through the use of a Virtual Private Network. Both the trusted network 28 and the open network 27 are based on the Transmission Control Protocol/Internet Protocol (TCP/IP) network communication protocols, although other communication protocols are possible. Other trusted and open network topologies and configurations are possible.

The RPD 17 can interrogate and program the PMDs 12-16, either through direct means, such as wired connectivity, or through indirect means, such as inductive coupled telemetry, optical telemetry, or selective radio frequency or wireless telemetry based on, for example, "strong" Bluetooth or IEEE 802.11 wireless fidelity "WiFi" and "WiMax" interfacing standards. Other forms of medical device interfacing are possible. In a further embodiment, the PMDs 12-16 are also remotely managed through the RPD 17, for example, such as described in commonly-assigned U.S. Patent application, entitled, "System and Method for Managing Alert Notifications in an Automated Patient Management System," Ser. No. 11/121,870, filed May 3, 2005, pending, the disclosure of which is incorporated by reference.

In a further embodiment, subjective impressions of personal wellness, which constitute qualitative data values, can be collected for post-programming considerations. For example, answers to health questions pertaining to patient well-being can be solicited from the patient 11 and collected following a change in PMD programming. To provide subjective impressions, the patient 11 would enter their data into a device that incorporates a user interface, such as a personal computer or telephone handset (not shown), or the RPD 17, if so equipped.

In a further embodiment, collected patient data can be evaluated by an RPD 17 or server 22, 24 for the occurrence of one or more chronic or acute health conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

In a still further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Structurally, the servers 22, 24 are server-grade computing platforms configured as a uni-, multi- or distributed processing systems, and the Web clients 18, 21 execute Web browser or equivalent applications on a general-purpose computing platform, such as a personal desktop or notebook computer, or other Web-enabled device. The servers 22, 24, Web clients 18, 21, and personal computer 34 that executes a dedicated application 20 include those components conventionally found in computing devices, such as, for example, a central processing unit (CPU), memory, network interface, persistent storage, and various components for interconnecting these components.

Data Flows

Generally, data is exchanged between the components of the regulated and non-regulated control zones in four phases. Briefly, during the first phase, a caregiver specifies remote programming instructions and accompanying parameters, using a data entry mechanism, that are subsequently translated into PMD-formatted commands to be validated by the caregiver, that is, either accepted or rejected, during the next phase. Upon acceptance, the PMD-formatted commands are provided to an RPD. The PMD-formatted commands are then verified and applied. The verification can be performed by the RPD, the PMD, or both devices. During the final phase, the PMD is interrogated to obtain physiometry following the remote programming. The phases are discussed in overview with reference to FIG. 2 and in further detail with reference to FIGS. 3-6.

Figure 2:
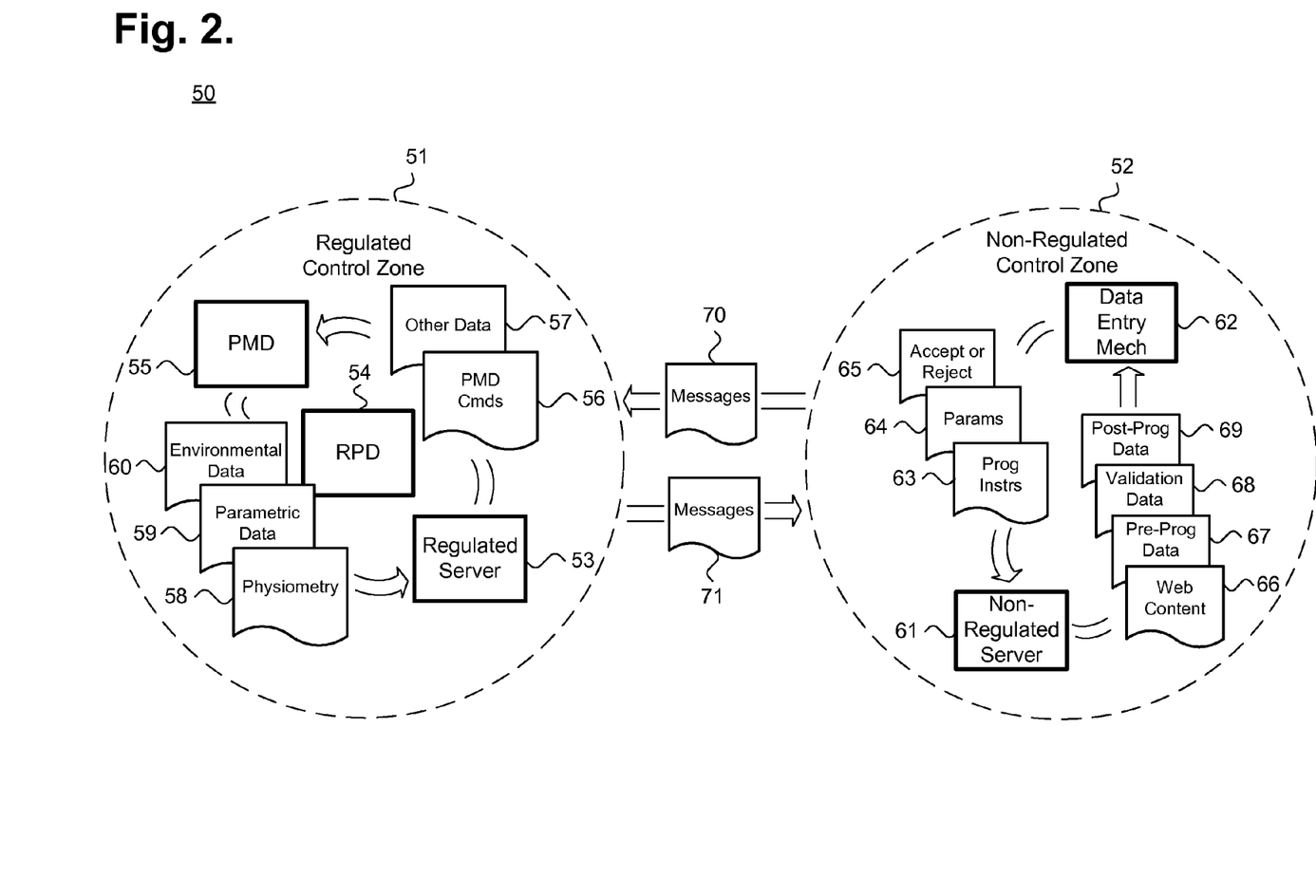
FIG. 2 is a data flow diagram showing overall data exchange between medically-regulated and non-regulated control zones.

To maintain control over compliance, data is passed between the control zones only via messages securely exchanged between the regulated and non-regulated servers. FIG. 2 is a data flow diagram showing overall data exchange 50 between regulated and non-regulated control zones 51, 52, respectively. Messages 70, 71 are received by the servers 53, 61, which process each message to determine the appropriate action to be taken.

As an overview, caregivers can remotely interrogate and program a PMD 55 using a data entry mechanism 62, which can be located in the non-regulated control zone 52 or, if performed on a regulated device (not shown), in the regulated control zone 51. Where the data entry mechanism 62 is a Web client, Web content 66 is provided to enable the data entry mechanism 62 to present the information formatted as a Web page.

Within the non-regulated control zone 52, the non-regulated server 61 provides PMD settings and patient physiology to the caregiver as pre-programming data 67. The caregiver can then specify programming instructions 63 and any accompanying parameters 64, which are forwarded to the regulated server 53 for translation into commands 56 formatted in PMD representation. The PMD-formatted commands 56 are provided back to the caregiver in displayable form as validation data 68, which the caregiver will accept or reject 65. The caregiver can also review post-remote programming IMD settings and patient data, which are provided by the non-regulated server 61 as post-programming data 69.

Within the regulated control zone 51, caregiver-specified programming instructions 63 and any accompanying parameters 64 are processed by the regulated server 53. The programming instructions 63 and parameters 64 are checked for correctness, as further described below with reference to FIG. 8, and translated into commands that are formatted for PMD representation 56. The PMD-formatted commands 56 are also digitally signed by the regulated server 53, which is a trusted server, to safeguard the transmittal of the commands to the RPD 54 and PMD 55. The digital signing allows an RPD 54, a PMD 55, or both devices, to verify the authenticity and integrity of the PMD-formatted commands 56. Authenticity confirms the identity of the source of the commands as legitimate, whereas integrity ensures that the commands were not altered during transit. Following digital signing, the commands are also committed to a secure storage.

Validation data 68 is created within the regulated control zone 51, and delivered to the non-regulated control zone 52 over the dedicated secure connection 33 for presentation to the caregiver.

Following caregiver approval, PMD-formatted commands 56 are delivered to and verified by the RPD 54, the PMD 55, or both devices. Verification includes checking the PMD-formatted commands 56 for authenticity and integrity. Only verified commands are applied to modify the programming of a PMD 55.

Finally, to effect remote programming, the RPD 54 applies the PMD-formatted commands 56 to the PMD 55, as well as any other data 57, such as interrogation commands or firmware patches. Following successful application, the RPD 54 can interrogate the PMD 55 to retrieve patient physiometry 58, parametric data 59, and, if applicable, environmental data 60, which are provided to the data entry mechanism 62 as the post-programming data 69 for confirmation of programming and caregiver review. In a further embodiment, the PMD 55 applies the PMD-formatted commands 56 itself, and can also autonomously provide the patient physiometry 58, parametric data 59, and, if applicable, environmental data 60.

Data Entry

Figure 3:
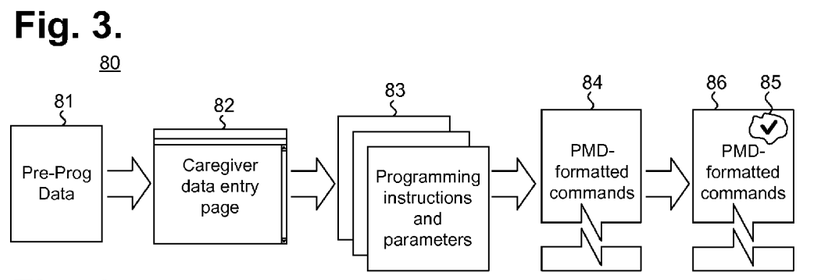
FIG. 3 is a data flow diagram showing caregiver data entry of remote programming instructions in the system of FIG. 1.

Caregivers can remotely interrogate or program a PMD by specifying programming instructions and any accompanying parameters using a data entry mechanism. FIG. 3 is a data flow diagram showing caregiver data entry 80 of remote programming instructions in the system 10 of FIG. 1. The data entry mechanism can either be within or outside of a regulated control zone. However, instructions originating from a data entry mechanism outside a regulated control zone must be coordinated through a regulated server, which performs correctness checking and digital signing.

For purposes of remote programming, caregivers are limited to a subset of programmable functions for a PMD that exclude those functions that can only be performed with the patient and caregiver in near physical proximity. The remaining set of "safe" functions is remotely programmable without worry of endangering the patient's safety. Additionally, programming instructions and associated parameters must be converted into commands formatted in PMD representation by a regulated server, or other regulated device capable of PMD-formatted command translation.

The remote programming can be applied to the PMD in either real time or deferred time. Real time remote programming involves an active connection between the data entry mechanism, the PMD, and each component situated in-between. From the perspective of the caregiver, the end-to-end remote programming operations underlying the specification of the programming instructions and parameters all the way through post-programming data review occur as a single session. Thus, a real time remote programming session is most similar to an in-clinic programming session, except for the distances possibly separating the caregiver from the patient and the slight additional latency time needed for command translations, correctness checking, data security, acceptance, and transmission. Deferred time remote programming, on the other hand, involves an intentional delay, that is, remote programming scheduled to be applied at a later time or time interval, or any delay that is longer that the minimal delay necessary to effect end-to-end real time remote programming.

Initially, current patient PMD settings and patient physiology are presented to the caregiver as pre-programming data 81. The pre-programming data 81 is incorporated into a caregiver data entry page 82, which may be a Web page or other representation for display to the caregiver on a data entry mechanism. The caregiver can specify remote programming instructions and any accompanying parameters 83.

To ensure patient safety, only safe remotely programmable functions are displayed through the data entry mechanism for caregiver selection. In a further embodiment, the safe programmable functions can further be limited to:

(1) Functions permitted if the PMD is in a particular state or mode;
(2) Parameters providing a subset of the range of functions allowed for any of the near proximity functions; or
(3) Preset commands, which may result in a programming of a collection of settings in the device together as a single unit.

In addition, for the parameters that limit selection to a functional subset of near proximity functions, the ranges can further be limited to a single direction, that is, strictly increasing or decreasing. Operationally, the data entry mechanism either limits selection to allowable programming instructions and parameters, or provides immediate feedback to the caregiver when an attempt to select a programming instruction or parameters is not allowed. Other limits on programming instruction and parameter selection are possible.

Figure 8:
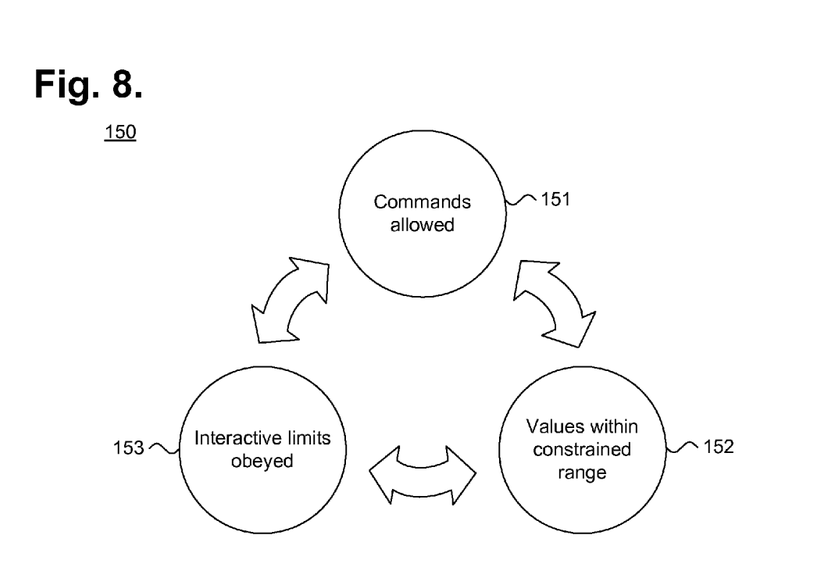
FIG. 8 is a process flow diagram showing remote programming correctness checking as performed in the method of FIG. 7.

Upon receipt, the regulated server translates the programming instructions and parameters 83 into PMD-formatted commands 84, which are checked for correctness, as further described below with reference to FIG. 8. Following correctness checking, the PMD-formatted commands are digitally signed 85 to create digitally-signed PMD-formatted commands 86, which are also committed into secure storage. If the remote programming is performed using a regulated data entry mechanism, such as a remotely-connectable programmer, the correctness checking and digital signing may be performed by the regulated data entry mechanism itself. Digital signing enables an RPD, a PMD, or both devices, to verify the authenticity and integrity of the commands.

Validation

Figure 4:
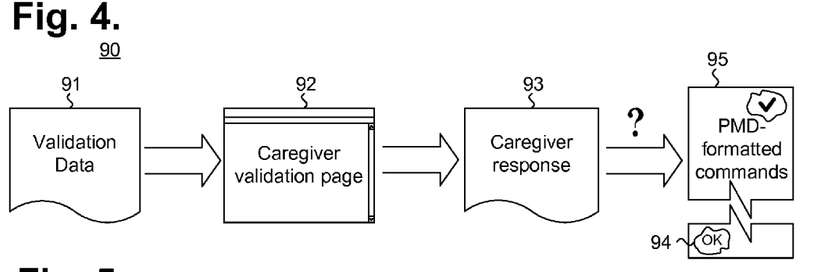
FIG. 4 is a data flow diagram showing caregiver remote programming instruction validation in the system of FIG. 1.

Programming instructions and associated parameters specified using a non-regulated data entry mechanism must be validated by caregivers to confirm correct translation into PMD representation. FIG. 4 is a data flow diagram showing caregiver remote programming instruction validation 90 in the system 10 of FIG. 1. The PMD-formatted commands 84 are reverse translated into validation data 91, which is incorporated into a caregiver validation page 92, which may be a Web page or other representation for display to the caregiver on a data entry mechanism. In one embodiment, the caregiver validation page 92 uses a simple "parameter : old value, new value" presentation format, although other formats are possible. Upon receipt, the caregiver indicates acceptance or rejection that is provided to the regulated server as the caregiver response 93, which is committed into secure storage. Upon acceptance, the regulated server marks 94 the digitally-signed PMD-formatted commands 86 (shown in FIG. 3) for delivery to the RPD associated with the PMD being remotely programmed to create digitally-signed and marked-for-delivery PMD-formatted commands, or simply "accepted" PMD-formatted commands 95. The mark 94 that indicates that the accepted PMD-formatted commands 95 are ready for delivery may be in the form of a digital signature. Digitally-signed PMD-formatted commands 86 that are not marked for delivery are not sent.

Other dispositions of the PMD-formatted commands pending caregiver approval are possible. For instance, the PMD-formatted commands 84 could be stored in the secure storage without first being digitally signed. The commands 84 would only be signed following caregiver approval and unsigned commands would not be sent. Alternatively, the PMD-formatted commands 84 could be digitally signed and stored in the secure storage, but would receive a second digital signature upon receiving caregiver approval. Commands not signed with the second digital signature would not be sent. Finally, the PMD-formatted commands 84 could be signed and stored in the secure storage. Upon receiving caregiver approval, the regulated server would check the digital signature and, if valid, would replace the original digital signature with a new digital signature. Commands not digitally signed for the second time would not be sent. Still other command dispositions are possible.

Verification and Application

Figure 5:
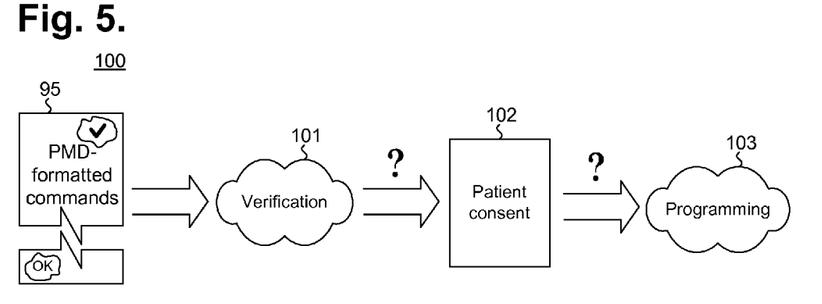
FIG. 5 is a data flow diagram showing verification and application of PMD-formatted commands in the system of FIG. 1.

The verification and application of the remote programming are performed independent of the devices used to enter, correctness check, and accept the programming. FIG. 5 is a data flow diagram showing verification and application 100 of the accepted PMD-formatted commands 95 in the system 10 of FIG. 1. The accepted PMD-formatted commands 95 are received by the RPD prior to the next interrogation session of the PMD. The accepted PMD-formatted commands 95 can either be pushed to the RPD by the regulated server or pulled by the RPD. Additionally, the regulated server and RPD interfacing can occur either on a scheduled basis, or upon demand. In a further embodiment, the accepted PMD-formatted commands 95 are received directly by the PMD using the same or similar form of interfacing to the regulated server or other regulated component.

Figure 9:
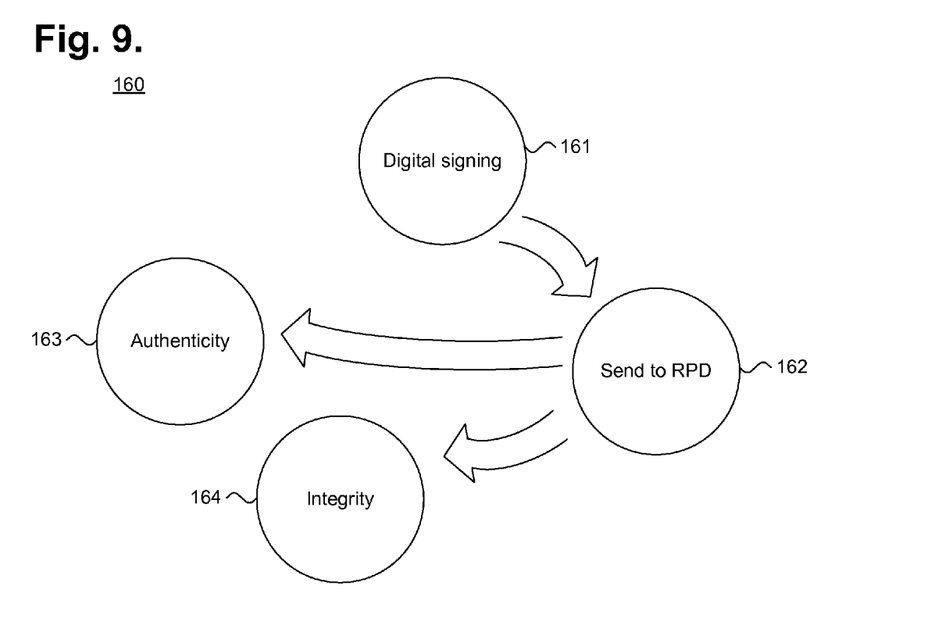
FIG. 9 is a process flow diagram showing verification of PMD-formatted commands as performed in the method of FIG. 7.

Upon receiving the accepted PMD-formatted commands 95, the RPD verifies 101 the digital signature, which verifies the authenticity, that is, source, of the commands, as well as the integrity of the commands, as further described below with reference to FIG. 9. In a further embodiment, the PMD itself can verify the authenticity and integrity of the commands, either in addition to or in lieu of the RPD. In a still further embodiment, the RPD can also check the accepted PMD-formatted commands 95 for staleness and redundancy, as further described below with reference to FIG. 10.

In contrast to a clinic or hospital setting in which patient consent can be implied by the near physical proximity of the caregiver and patient, remote programming requires some explicit form of patient consent 102. Patient consent 102 can be confirmed through several approaches, including:

(1) The RPD can prompt the patient to hit a button or similar control on a user interface to signify consent;
(2) The caregiver can manually notify the patient that new programming is available for their PMD and the patient can initiate a programming session through interaction with the PMD;
(3) The PMD itself can prompt the patient, for example, in conjunction with an interrogation session to retrieve stored patient data; and
(4) Patient consent may be granted prior to the beginning of the remote programming operation and stored in the secure storage. The regulated server can confirm the prior patient consent before sending the accepted PMD formatted commands 95 to the RPD. In a further embodiment, the prior patient consent can be included within the accepted PMD-formatted commands 95, where the prior patient consent can be used by the RPD prior to initiating a remote programming session with the PMD.

Other forms of confirming patient consent 102 are possible.

Once patient consent has been confirmed, the RPD undertakes actual programming 103 by applying the accepted PMD-formatted commands 95 to the PMD during a programming session. The accepted PMD-formatted commands 95 can be applied through short range telemetry, such as inductive telemetry using a wand physically connected to the RPD, or through long range telemetry, such as RF telemetry, which only requires near physical patient proximity to the RPD. In a further embodiment, authentication through induction or other form of short range telemetry, or physical communications or interface, may be necessary prior to commencing a programming session through long range telemetry, such as described in commonly-assigned U.S. patent application Ser. No. 10/800,806, filed Mar. 15, 2004, pending, and U.S. patent application Ser. No. 10/801,150, filed Mar. 15, 2004, pending, the disclosures of which are incorporated by reference.

The programming is transacted in a single session. If the programming session is interrupted, such as by the patient moving out of range or dropping the wand, the patient may be prompted to resume the session. If required, upon obtaining a response from the patient to resume the session, the RPD will retry applying the programming by automatically resuming the session if the interruption has only been for a short duration. If prior patient consent has already been obtained, the RPD can automatically retry without having to first prompt the patient. However, if the patient either ignores the prompt or the interruption continues for a long duration, the programming session is halted and earlier PMD programmed state is restored.

Confirmation

Figure 6:
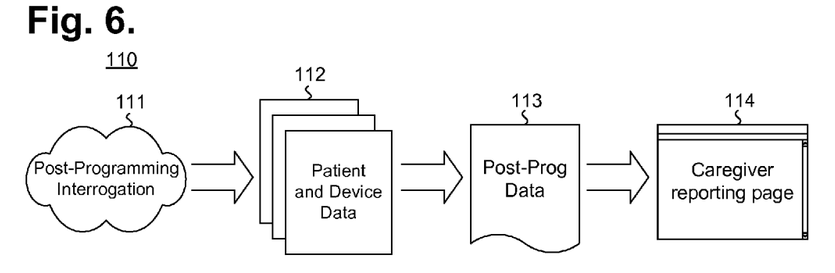
FIG. 6 is a data flow diagram showing post-remote programming reporting in the system of FIG. 1.

Programming can be confirmed and effectiveness can be evaluated by interrogating the PMD following a remote programming session. FIG. 6 is a data flow diagram showing post-remote programming reporting 110 in the system 10 of FIG. 1. Following completion of a programming session, the RPD can interrogate 111 the PMD to retrieve patient and device data 112, which are provided by the non-regulated server as post-programming data 113 and is committed to the secure storage. The post-programming data 113 is incorporated into a caregiver reporting page 114, which may be a Web page or other representation for display to the caregiver on a data entry mechanism. In a further embodiment, the patient can provide qualitative patient data through a user interface of the RPD or other patient-operable device to provide subjective feedback following application of the accepted PMD-formatted commands 95.

Remote Programming Method

Figure 7:
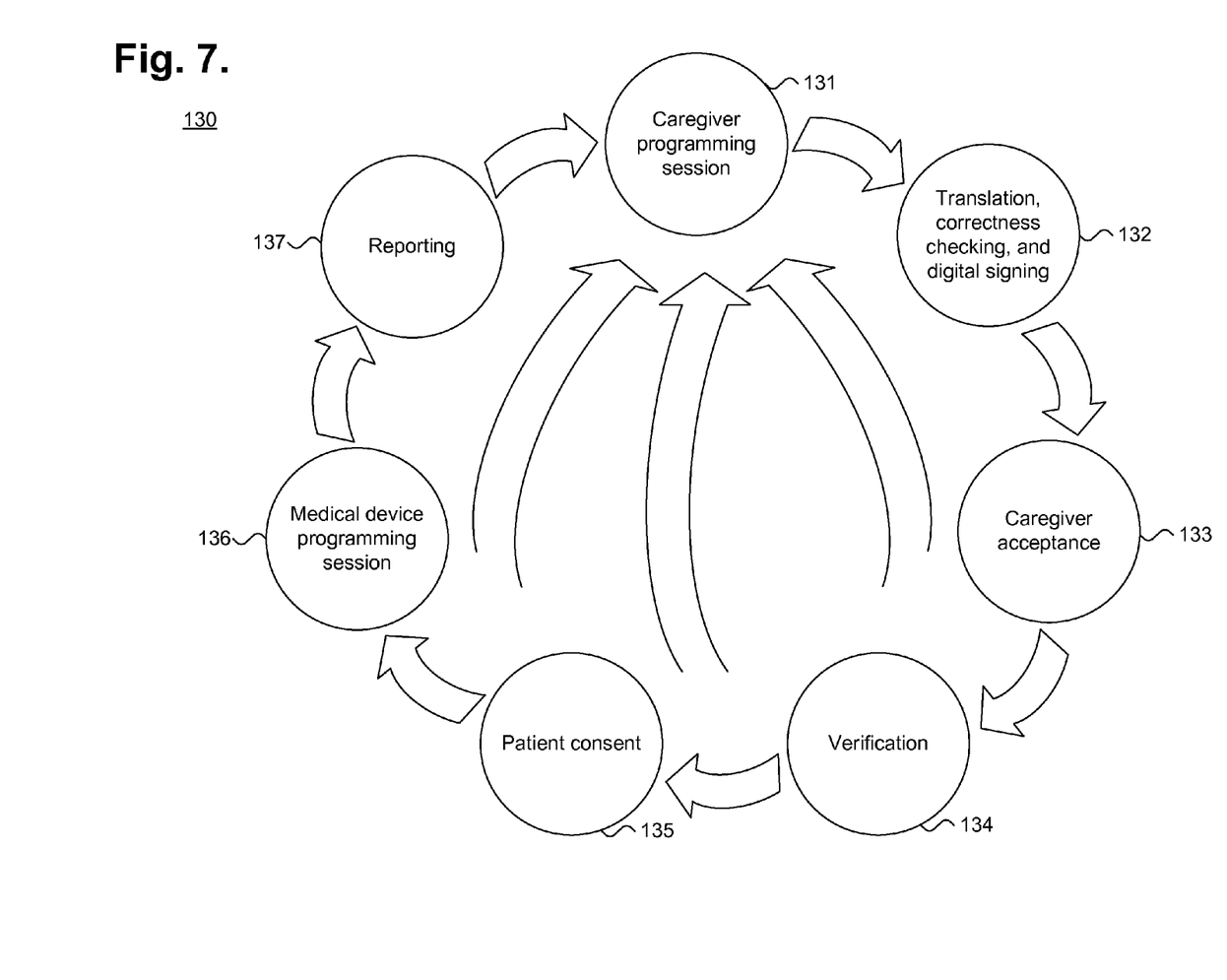
FIG. 7 is a process flow diagram showing a method for remotely programming a patient medical device, in accordance with one embodiment.

Remote programming is initiated by caregiver action and ends with the reporting of the success or failure of the application of the programming to the intended PMD back to the caregiver. FIG. 7 is a process flow diagram showing a method 130 for remotely programming a patient medical device, in accordance with one embodiment. Remote programming is performed as a sequence of operations, which, in specific instances, can be suspended or broken at specific points as necessary.

Initially, a caregiver performs a remote programming session (operation 131) through a data entry mechanism. Caregiver-selected programming instructions and parameters are translated by a regulated server into PMD-formatted commands, which are checked for correctness and digitally signed (operation 132). The PMD-formatted commands are also reverse translated and provided to the caregiver in displayable form for acceptance or rejection (operation 133). If the translated programming is rejected by the caregiver, control reverts back to the caregiver programming session (operation 131). Otherwise, the PMD-formatted commands are marked for delivery to the RPD and, following receipt by the RPD, are verified for authenticity and integrity (operation 134). In a further embodiment, the PMD itself also performs verification of the commands, either in addition to or in lieu of the RPD. Assuming the commands are verified, the patient consent is confirmed (operation 135) prior to application of the commands. However, if the patient does not provide consent, control again reverts back to the programming session (operation 131). Upon consent, the RPD performs a programming session (operation 136). If the session is interrupted and not resumed, or abnormally terminates, the original PMD programming is restored and control reverts back to the programming session (operation 131). Upon successful programming, the RPD interrogates the PMD following programming session completion to report post-programming results to the caregiver (operation 137) for review and evaluation.

Correctness Checking

Caregiver-specified programming instructions and any accompanying parameters must be checked for correctness prior to being applied to a PMD in a remote programming session, both to determine that only permitted settings have been specified and to ensure medical-regulatory compliance. FIG. 8 is a process flow diagram showing programming correctness checking 150 as performed in the method 130 of FIG. 7. All programming instructions and parameters must be checked for correctness. Regulated data entry mechanisms, such as a remotely-connectable programmer, are capable of performing full correctness checks and of generating PMD-formatted commands directly. However, programming instructions and parameters originating from a non-regulated data entry mechanism must be checked by a regulated server or equivalent component. As a result, caregiver-specified programming instructions and accompanying parameters are provided to the regulated server as caregiver data selections, which are translated into PMD-formatted commands and checked for correctness, which includes checking.

(1) Whether the commands are allowed, that is, patient safe and permitted to be specified remotely (operation 151);
(2) That the values of any parameters are within appropriate constraint range (operation 152); and
(3) That the commands obey any interactive limits, that is, that the commands, in combination with other commands and the current state of the PMD, result in a state that is safe to the patient (operation 153).

Other forms of correctness checks are possible.

Verification

Remote programming requires transfer of PMD-formatted commands over a network or other interconnection, which creates a possibility of compromise or corruption. The PMD-formatted commands are safeguarded using digital signing at the source, which is a regulated server for programming originating from a non-regulated data entry mechanism, or a regulated data entry mechanism, such as a programmer. FIG. 9 is a process flow diagram showing verification 160 of PMD-formatted commands as performed in the method 130 of FIG. 7. Following correctness checking and caregiver acceptance, the PMD-formatted commands 56 are digitally signed (operation 161) by the regulated server 53, if remote programming was performed using a non-regulated data entry mechanism. Otherwise, the digital signing may be performed by the regulated data entry mechanism. In one embodiment, a 2048-bit asymmetric RSA keys with an SHA-1 hashing algorithm is used for digital signing, although other forms of digital signing are possible. Once marked for delivery, the digitally signed PMD-commands are sent to the RPD associated with the PMD being remotely programmed (operation 162). Upon receipt, the digitally signed PMD-formatted commands are verified by the RPD, the PMD, or both devices, before being applied. Verification includes determining their authenticity (operation 163) which includes ascertaining their source as being an authorized regulated server or other authorized regulated device, and confirming their integrity (operation 164). Other types of verification are possible.

Staleness and Redundancy Checking

Figure 10:
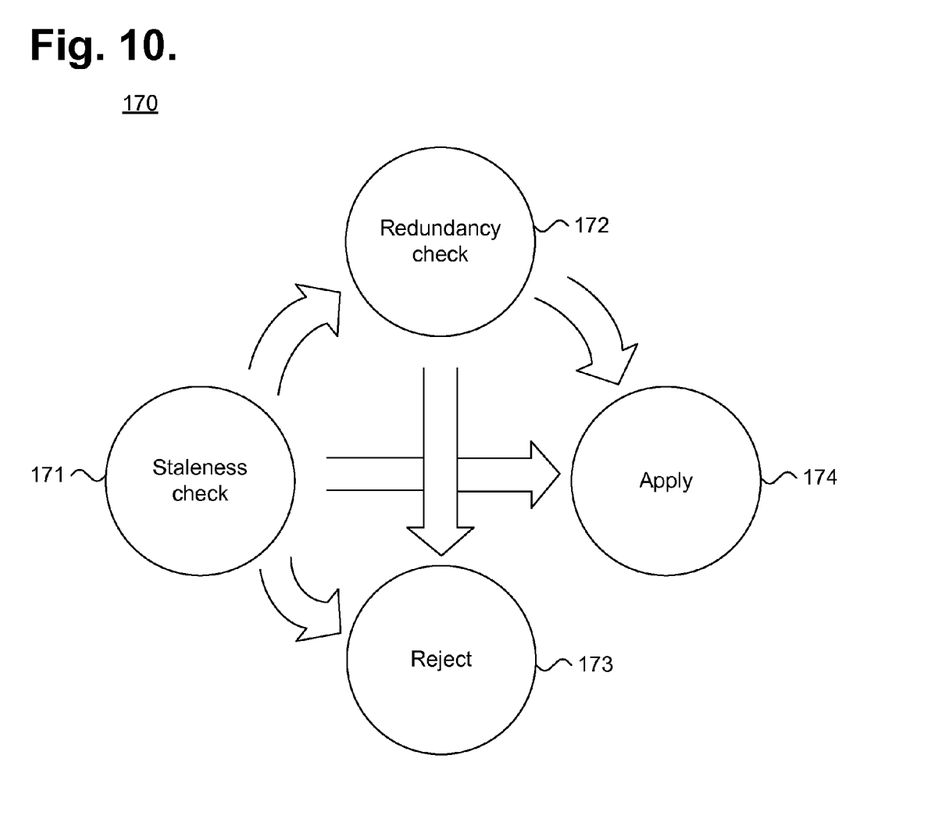
FIG. 10 is a process flow diagram showing staleness checking as performed in a further embodiment of the method of FIG. 7.

Remote programming introduces a delay between the time that new PMD programming is specified and the time that the resulting PMD-formatted commands are actually applied to the PMD. Delay can cause the programming to become stale or redundant in light of intervening events, such as PMD programming in a clinic or hospital setting. FIG. 10 is a process flow diagram showing staleness checking 170 as performed in a further embodiment of the method 130 of FIG. 7. Following correctness checking and caregiver acceptance, accepted PMD-formatted commands 95 can be supplemented with an expiration time, that is, a "staleness" check (operation 171) that sets a time after which this particular programming must be rejected (operation 173) and not be applied (operation 174).

The accepted PMD-formatted commands 95 can also be checked for redundancy prior to application (operation 172). A timestamp that indicates when the PMD was last programmed can be saved by the PMD. This "last programming" timestamp can be provided as part of the pre-programming data 67 (shown in FIG. 2) that is supplied to a caregiver for review and consideration when entering programming instructions and parameters on a data entry mechanism. That particular last programming timestamp is then included with any subsequently generated accepted PMD-formatted commands 95. Prior to being applied to the PMD, the last programming timestamp included with the commands 95 is checked against the last programming timestamp currently stored on the PMD. If the timestamps do not match, this particular programming must be rejected as redundant (operation 173) and not be applied (operation 174). Other forms of staleness and redundancy checking are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for remotely programming a patient medical device (PMD), comprising:
    a non-regulated user interface configured to receive caregiver-selected programming instructions, wherein the non-regulated user interface is configured to limit the selection of programming instructions to a subset of all possible PMD instructions that are appropriate for programming remotely;
    a regulated device configured to translate the caregiver-selected programming instructions specified remotely at the non-regulated user interface into commands formatted for the patient medical device to control functionality thereof, and to check correctness of the PMD-formatted commands;
    a signing device to digitally sign the PMD-formatted commands prior to transmittal; and
    a remote programming device configured to control application of the PMD-formatted commands to the PMD during a programming session initiated and performed remotely, wherein the remote programming device confirms application of the PMD-formatted commands through interrogation of the PMD to verify the functionality modified.

2. A system according to claim 1, wherein the PMD-formatted commands are applied by the remote programming device to the PMD in one of deferred time and real time.

3. A system according to claim 1, wherein the regulated device is configured to confirm validity of the PMD-formatted commands as part of the correctness checking by performing at least one of the checks selected from the group consisting of:
    ensuring that the PMD-formatted commands are allowed;
    verifying that any values included as part of the PMD-formatted commands are within constrained parameter limits; and checking the PMD-formatted commands against existing PMD commands and PMD state for any interactive limits.

4. A system according to claim 1, a security infrastructure configured to ensure transmittal of the PMD-formatted commands, comprising:
a signing device to digitally sign the PMD-formatted commands prior to transmittal; and
a verifier to confirm an identity of a source of the PMD-formatted commands as legitimate and to ensure the PMD-formatted commands were not altered during transit following transmittal.

5. A system according to claim 4, wherein the verifier comprises at least one selected from the group consisting of: the remote programming device and the PMD.

6. A system according to claim 1, further comprising:
an approval mechanism to receive caregiver approval of the PMD-formatted commands; and
a secure storage, configured to store PMD-formatted commands-having a disposition selected from the group consisting of:
a first disposition in which the PMD-formatted commands are digitally signed, stored in the secure storage, and configured to be marked for delivery only following receipt of the caregiver approval;
a second disposition-in which the PMD-formatted commands are configured to be digitally signed for delivery only following receipt of caregiver approval;
a third disposition-in which the PMD-formatted commands are digitally signed, and configured to be digitally signed again, and further configured to be marked for delivery only upon having two digital signatures; and
a fourth disposition-in which the PMD-formatted commands are digitally signed, configured to be checked for validity of the digital signature following receipt of the caregiver approval, further configured to be digitally signed in place of the existing digital signature, and further configured to be marked for delivery only upon having a second digital signature.

7. A system according to claim 1, further comprising:
an expiration time associated with the PMD-formatted commands, wherein the regulated device is configured to apply the expiration time to the PMD-formatted commands.

8. A system according to claim 1, further comprising:
an included timestamp to indicate a time that the PMD was last programmed prior to translation of the programming instructions, wherein the timestamp is included with the PMD-formatted commands; and
a timestamp stored on the PMD to indicate a time that programming was most recently applied to the PMD, wherein the application of the PMD-formatted commands is conditioned subject to the included timestamp matching the stored timestamp.

9. A system according to claim 1, further comprising:
a data entry mechanism to specify the programming instructions using at least one selected from the group consisting of: a Web browser application, a remotely-connectable programmer, and a dedicated application on a personal computer.

10. A system according to claim 1, further comprising:
a patient consent mechanism to confirm the patient consent through at least one selected from the group consisting of: prompting by a programming device, patient-initiated action, prompting by the PMD, and prior patient consent.

11. A system according to claim 1, wherein the application of the PMD-formatted commands is performed in a single programming session, comprising at least one selected from the group consisting of:
a user interface to prompt for resumption of the programming session in response to an short-duration interruption;
a retry mechanism to automatically resume the programming session after a short duration interruption; and
a recovery mechanism to halt the programming session and to restore earlier PMD-formatted commands to the PMD in response to a long-duration interruption.

12. A system according to claim 1, wherein the PMD comprises at least one selected from the group consisting of: an implantable PMD and an external PMD.

13. A method for remotely programming a patient medical device (PMD), comprising:
receiving caregiver-selected programming instructions at a non-regulated user interface, wherein the non-regulated user interface limits the selection of programming instructions to a subset of all possible PMD instructions that are appropriate for programming remotely;
translating by a regulated device caregiver-selected programming instructions specified remotely at the non-regulated user interface into commands formatted for the patient medical device to control functionality thereof;
checking correctness of the PMD-formatted commands;
prior to transmittal, digitally signing the PMD-formatted commands;
controlling application of the PMD-formatted commands to the PMD during a programming session initiated and performed remotely; and
confirming the application of the PMD-formatted commands through interrogation of the PMD to verify the functionality modified.

14. A method according to claim 13, wherein the PMD-formatted commands are applied to the PMD in one of real time or deferred time.

15. A method according to claim 13, further comprising:
confirming validity of the PMD-formatted commands as part of the correctness checking, further comprising at least one selected from the group consisting of:
ensuring the PMD-formatted commands are allowed;
verifying that any values included as part of the PMD-formatted commands are within constrained limits; and
performing interactive limit checking of the PMD-formatted commands against existing PMD commands and state.

16. A method according to claim 13, further comprising ensuring secure-transmittal of the PMD-formatted commands, comprising:
prior to transmittal, digitally signing the PMD-formatted commands, and following transmittal, confirming an identify of a source of the PMD-formatted commands as legitimate and ensuring that the PMD-formatted commands were not altered during transit.

17. A method according to claim 13, further comprising:
receiving caregiver approval of the PMD-formatted commands; and
maintaining a secure storage, further comprising at least one of the elements selected from the group consisting of:
providing a security scheme in which the PMD-formatted commands are digitally signed, stored in the secure storage, and marked for delivery only following receipt of the caregiver approval;

providing a security scheme in which the PMD-formatted commands are stored in the secure storage, and digitally signed for delivery only following receipt of caregiver approval;

providing a security scheme in which the PMD-formatted commands are digitally signed, stored in the secure storage, digitally signed again, and marked for delivery only upon having two digital signatures; and providing a security scheme in which the PMD-formatted commands are digitally signed, stored in the secure storage, checked for validity of the digital signature following receipt of the caregiver approval, digitally signed in place of the existing digital signature, and marked for delivery only upon having a second digital signature.

18. A method according to claim 13, further comprising:

including a timestamp with the PMD-formatted commands to indicate a time that the PMD was last programmed prior to translation of the programming instructions;

storing a timestamp on the PMD to indicate a time that programming was most recently applied to the PMD; and conditioning the application of the PMD-formatted commands subject to the included timestamp matching the stored timestamp.

19. A non-transitory computer-readable storage medium holding code for performing the method according to claim 13.

20. An apparatus for remotely programming a patient medical device (PMD), comprising:

means for receiving caregiver-selected programming instructions at a non-regulated user interface, wherein the non-regulated user interface is configured to limit the selection of programming instructions to a subset of all possible PMD instructions that are appropriate for programming remotely;

means for translating by a regulated device the caregiver-selected programming instructions specified remotely at the non-regulated user interface into commands formatted for the patient medical device to control functionality thereof;

means for checking correctness of the PMD-formatted commands;

means for digitally signing the PMD-formatted commands prior to transmittal;

means for controlling application of the PMD-formatted commands to the PMD during a programming session initiated and performed remotely; and means for confirming the application of the PMD-formatted commands through interrogation of the PMD to verify the functionality modified.

* * * * *